US00PP08560P

United States Patent [19]

Higgins

[11] Patent Number: Plant 8,560

[45] Date of Patent: Jan. 25, 1994

[54] SALVIA PLANT NAMED 'VARIEGATA'

[75] Inventor: Richard Higgins, Phoenix, Ariz.

[73] Assignee: Canterbury Enterprises, Inc., Phoenix, Ariz.

[21] Appl. No.: 895,501

[22] Filed: Jun. 8, 1992

[51] Int. Cl.[5] ..... A01H 5/00

[52] U.S. Cl. ..... Plt./54.1

[58] Field of Search ..... Plt. 68.1, 54.1

[56] References Cited

PUBLICATIONS

Bailey, L. H., "Salvia: 35. Greggii" *The Standard Cyclopedia of Horticulture* 1935 The Macmillan Company, p. 3063.

*Primary Examiner*—James R. Feyrer

*Attorney, Agent, or Firm*—Townsend and Townsend Khourie and Crew

[57] ABSTRACT

This disclosure relates to a new and unique member of *Salvia greggii* which occured as a spontaneous mutant on a specimen plant which was being used for asexual propagation of nursery stock in Phoenix, Ariz. This plant, while generally similar to the phenotype of the unnamed parent plant, differs from the parent plant and other plants of the species by having a distinctive marginal variegation which is confined to the foliage of the disclosed plant.

1 Drawing Sheet

BACKGROUND OF THE PLANT

The present invention relates to a new variety of *Salvia greggii*. For purposes of international recognition, the varietal or market name (determination) is 'Variegata'. DESERT BLAZE TM is an associated trademark of the variety of identify its source of origin. 'Variegata' originated as a sported part of a plant in monoculture at Phoenix, Ariz., in July, 1990. It was taken from a production block of *Salvia greggii* and maintained for asexual propagation purposes. This plant was selected from other plants because its leaves were variegated. The variegation is a clearly defined two-color (green-white) display without noticeable gradations of color. No other plant parts display this trait. The variegation distinguishes this new plant from other *S. greggii* plants, none of which are variegated.

Asexual propagation of this plant was carried out at Phoenix, Ariz., by cuttings through several generations. The novel leaf color was demonstrated as firmly fixed and remaining true from generation to generation.

The vigor of the 'Variegatta' is unchanged from its wild-type parental variety. Its growth habit does not noticeably differ from its wild-type parental variety. The parental variety had no known designation.

The following is a detailed description of my new *Salvia greggii* plant based upon observation of plants grown at Phoenix, Ariz., the color designations being according to The R.H.S. Color Chart published by The Royal Horticultural Society of London, England.

DESCRIPTION OF THE DRAWING

This new variety is illustrated by the accompanying photographic drawing (FIG. 1.) which shows its bloom and leaves in full color, with such colors of the photograph being as true to those of the plant as can be reasonably obtained from conventional professional photographic procedures. The raceme depicted in the drawing is not fully mature. As the action progresses this raceme will elongate to between 10 and 15 cm.

DESCRIPTION OF THE PLANT

Figure 1:
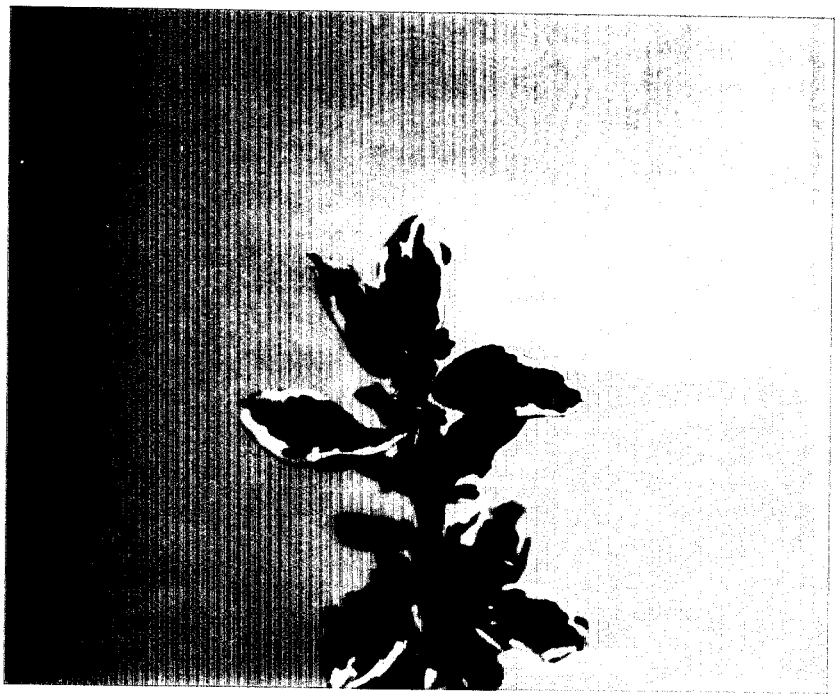

Plant form: Bush.
Plant height: To one meter.
Plant growth habit: Perennial.
Leaf arrangement: Opposite.
Leaf shape: Elliptic to oblong.
Leaf length: 1.2–3.0 centimeters.
Leaf width: 0.4–1.6 centimeters.
Leaf blade margin: Entire to crenulate.
Leaf blade thickness: Slightly fleshy.
Leaf blade venation: Scarcely visible.
Leaf blade color: Yellow-green RHS 147B.
Leaf blade color variegation: Present in a clearly delineated two-tone display.
Leaf blade margin color: Yellow RHS 9D.
Leaf blade apex: Acute or obtusely rounded.
Leaf blade apex color: Yellow RHS 9D.
Leaf blade base: Rounded to acuminate, sometimes oblique.
Leaf blade base color: Yellow-green RHS 147B.
Petiole shape: Wing-like.
Petiole length: 3–9 millimeters.
Petiole width: 0.5–1.0 millimeter.
Petiole color: Yellow-green RHS 147B.

DESCRIPTION OF THE FLOWER

Inflorescence type: Terminal raceme.
Inflorescence length: 10–15 centimeters.
Flower number: To 15 decussate pairs.
Flower shape: Tubular, two-lipped.
Pedicel length: 3–6 millimeters.
Pedicel width: 0.5–0.8 millimeters.
Pedicel pubescence: Glandular, puberulent.
Pedicel color: Purplish RHS 78B.
Calyx shape: Broadly campanulate, flared toward the apex.
Calyx rib number: 10, longitudinal.
Calyx length: 14 millimeters.
Calyx width: To 6 millimeters.
Calyx pubescence: Glandular, puberulent.
Calyx color: Purplish RHS 78B.
Calyx lobe number: 3.

Calyx upper lobe number: 1.
Calyx upper lobe shape: Acute.
Calyx upper lobe length: 5 millimeters.
Calyx upper lobe width: 6 millimeters.
Calyx lower lobe number: 2.
Calyx lower lobes shape: Acute.
Calyx lower lobes length: 3 millimeters.
Calyx lower lobes width: 4 millimeters.
Corolla shape: Tubular proximally to two-lipped distally.
Corolla length: 2.5–3.0 centimeters.
Corolla color: Red RHS 45B.
Corolla tube length: 15 millimeters.
Corolla tube width: 3 millimeters.
Corolla tube depth: 6 millimeters.
Corolla tube lip number: 2.
Corolla upper lip number: 1.
Corolla upper lip shape: Hood-like.
Corolla upper lip length: 9 millimeters.
Corolla lower lip number: 2 suborbicular.

Corolla lower lip shape: Banner-like, extended downward.
Corolla lower lip outline: Obovate.
Corolla lower lip length: 12 millimeters.
Corolla lower lip diameter at tip: 7 millimeters.

DESCRIPTION OF REPRODUCTIVE ORGANS

Style length: 3.0–3.5 centimeters.
Style pubescence: Present toward tip.
Style attachment site: To a four-lobed ovary between the lobes.
Stamen number: 2.
Stamen shape: Seesaw-like.
Filament length: 4 millimeters.
Connective length: 14 millimeters.
Anther attachment site: Outer end of the connective.
Fertility: Unobserved.

What is claimed is:

1. The new distinct variety of *Salvia greggii* herein described and illustrated and identified by the characteristics enumerated above.

* * * * *